US012797058B2

(12) United States Patent
Jee

(10) Patent No.: US 12,797,058 B2
(45) Date of Patent: Nov. 17, 2026

(54) EYELID SPECULUM

(71) Applicant: THE CATHOLIC UNIVERSITY OF KOREA INDUSTRY-ACADEMIC COOPERATION FOUNDATION, Seoul (KR)

(72) Inventor: Dong Hyun Jee, Seoul (KR)

(73) Assignee: THE CATHOLIC UNIVERSITY OF KOREA INDUSTRY-ACADEMIC COOPERATION FOUNDATION, Seoul (KR)

(*) Notice: Subject to any disclaimer, the term of this patent is extended or adjusted under 35 U.S.C. 154(b) by 13 days.

(21) Appl. No.: 19/001,104

(22) Filed: Dec. 24, 2024

(65) Prior Publication Data

US 2025/0127502 A1 Apr. 24, 2025

Related U.S. Application Data

(63) Continuation of application No. PCT/KR2024/008790, filed on Jun. 25, 2024.

(30) Foreign Application Priority Data

Jul. 12, 2023 (KR) ........................ 10-2023-0090342

(51) Int. Cl.
*A61B 17/02* (2006.01)

(52) U.S. Cl.
CPC ...... *A61B 17/0231* (2013.01); *A61B 17/0206* (2013.01)

(58) Field of Classification Search
CPC ........................ A61B 17/0231; A61B 17/0206
See application file for complete search history.

(56) References Cited

U.S. PATENT DOCUMENTS 5,341,798 A 8/1994 Grounauer
5,618,261 A * 4/1997 Nevyas .............. A61B 17/0231 606/107

(Continued)

FOREIGN PATENT DOCUMENTS

CN 204293347 U 4/2015
CN 209236242 U 8/2019

(Continued)

OTHER PUBLICATIONS

Office Action issued in KR 10-2023-0090342; mailed by the Korean Ministry of Intellectual Property on Apr. 16, 2025.

(Continued)

*Primary Examiner* — Ellen C Hammond
(74) *Attorney, Agent, or Firm* — Studebaker Brackett PLLC

(57) ABSTRACT

Disclosed is an eyelid speculum including a frame, a first rotary arm coupled to one side of the frame to be rotatable, a second rotary arm coupled to an opposite side of the frame to be rotatable, a movement part configured to move the first rotary arm and the second rotary arm such that the first rotary arm and the second rotary arm are moved in a direction, in which they become closer to or more distant from each other, a first support arm coupled to the first rotary arm to be rotatable, and configured to support an upper eyelid, and a second support arm coupled to the second rotary arm, and configured to support a lower eyelid.

3 Claims, 7 Drawing Sheets

(56) References Cited

U.S. PATENT DOCUMENTS

| | | | | |
|---|---|---|---|---|
| 6,283,913 | B1 * | 9/2001 | Seibel | A61B 17/0231 600/219 |
| 2015/0305732 | A1 * | 10/2015 | Dahl | A61B 17/02 600/219 |
| 2022/0322931 | A1 | 10/2022 | Koh | |

FOREIGN PATENT DOCUMENTS

| | | | |
|---|---|---|---|
| CN | 210990471 | U | 7/2020 |
| CN | 112472169 | A | 3/2021 |
| CN | 215191884 | U | 12/2021 |
| CN | 215535575 | U | 1/2022 |
| CN | 114027901 | A | 2/2022 |
| CN | 216824521 | U | 6/2022 |
| CN | 218128617 | U | 12/2022 |
| JP | 2020-124330 | A | 8/2020 |
| KR | 10-2021-0030123 | A | 3/2021 |

OTHER PUBLICATIONS

International Search Report issued in PCT/KR2024/008790; mailed Oct. 21, 2024.

Australian Examination Report No. 1, Australian Patent Application No. 2024278438, dated Jun. 16, 2026.

* cited by examiner

EYELID SPECULUM

CROSS-REFERENCE TO RELATED APPLICATIONS

The present application is a continuation of International Patent Application No. PCT/KR2024/008790, filed on Jun. 25, 2024, which is based upon and claims the benefit of priority to Korean Patent Application No. 10-2023-0090342 filed on Jul. 12, 2023. The disclosures of the above-listed applications are hereby incorporated by reference herein in their entirety.

BACKGROUND

Embodiments of the present disclosure described herein relate to an eyelid speculum.

An eye surgery refers to a surgery on an eye or its appendages, which is performed by an ophthalmologist. An eye is a vulnerable organ, and an extreme care is required before and after a surgery.

During an eye surgery, an upper eyelid and a lower eyelid are widened by using an eyelid speculum. The eyelid speculum may have two metal bars that are inserted into a center of an eyeball and widen the upper eyelid and the lower eyelid, respectively.

However, according to the existing eyelid speculum, when the two metal bars are inserted into an inside of the upper eyelid and an inside of the lower eyelid, respectively and then are discharged, a cornea may be damaged as the two metal bars contact the cornea of the eyeball or press the cornea of the eyeball.

In addition, according to the existing speculum, when the two metal bars supported by the upper eyelid and the lower eyelid are moved in a direction, in which the upper eyelid and the lower eyelid are widened, the metal bar that widens the upper eyelid presses the upper eyelid against a frontal bone because the movement directions of the two metal bars are parallel to the face. As a result, the upper eyelid levator muscle is crushed and damaged by the metal bar that widen the upper eyelid against the frontal bone, and thus, ptosis is caused.

Here, ptosis is a disease, in which the upper eyelid descends and covers the eyeball, and as the upper eyelid covers the eyeball, it is not aesthetically pleasing, and in severe cases, it may obscure the visual axis of the eyeball, and thus, the vision may be decreased.

In addition, according to the existing speculum, when the two metal bars supported by the upper eyelid and the lower eyelid are moved in a direction, in which of the upper eyelid and the lower eyelid are widened, the two metal bars are separated from the upper eyelid and the lower eyelid because the movement directions of the two metal bars are parallel to the face.

SUMMARY

Embodiments of the present disclosure provide an eyelid speculum that may prevent damage to a cornea and ptosis.

Problems to be solved by the present disclosure are not limited to the problems mentioned above, and other problems that are not mentioned will be clearly understood by those skilled in the art from the following description.

An eyelid speculum according to an embodiment of the present disclosure includes a frame, a first rotary arm coupled to one side of the frame to be rotatable, a second rotary arm coupled to an opposite side of the frame to be rotatable, a movement part configured to move the first rotary arm and the second rotary arm such that the first rotary arm and the second rotary arm are moved in a direction, in which they become closer to or more distant from each other, a first support arm coupled to the first rotary arm to be rotatable, and configured to support an upper eyelid, and a second support arm coupled to the second rotary arm, and configured to support a lower eyelid.

Furthermore, the eyelid speculum may further include a first hinge part coupling the first support arm such that the first support arm is relatively rotated in a circumferential direction of the first rotary arm with respect to the first rotary arm, and a second hinge part coupling the second support arm such that the second support arm is relatively rotated in a circumferential direction of the second rotary arm with respect to the second rotary arm.

Furthermore, the eyelid speculum may further include a first locking part configured to lock or unlock the first support arm to or from the first rotary arm, and a second locking part configured to lock or unlock the second support arm to or from the second rotary arm.

Furthermore, the first support arm may include a first connection part coupled to the first rotary arm to be rotatable, and a first curved part extending from the first connection part in an arc shape, and inserted into an inside of the upper eyelid to support the upper eyelid, and the second support arm may include a second connection part coupled to the second rotary arm to be rotatable, and a second curved part extending from the second connection part in an arc shape, and inserted into an inside of the lower eyelid to support the lower eyelid.

Furthermore, when the first curved part and the second curved part are inserted into the inside of the upper eyelid and the inside of the lower eyelid, respectively, the first curved part may be rotated to be aligned on the inside of the upper eyelid and the second curved part may be rotated to be aligned on the inside of the lower eyelid.

Furthermore, a plurality of first curved parts may be provided, and the plurality of first curved parts may be arranged along the first connection part, and a plurality of second curved parts may be provided, and the plurality of second curved parts may be arranged along the second connection part.

Furthermore, the eyelid speculum may further include a guide rail configured to, when the first curved part and the second curved part are moved to widen or gather the upper eyelid and the lower eyelid, guide movement paths of the first connection part and the second connection part to a guide in an arc shape corresponding to a circumference of an eyeball such that the first curved part and the second curved part are moved along the circumference of the eyeball.

Furthermore, the guide rail may include a rail body, and a rail hole formed to pass through the rail body in an arc shape, and into which the first connection part and the second connection part are inserted.

Other details of the present disclosure are included in the detailed description and the drawings.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
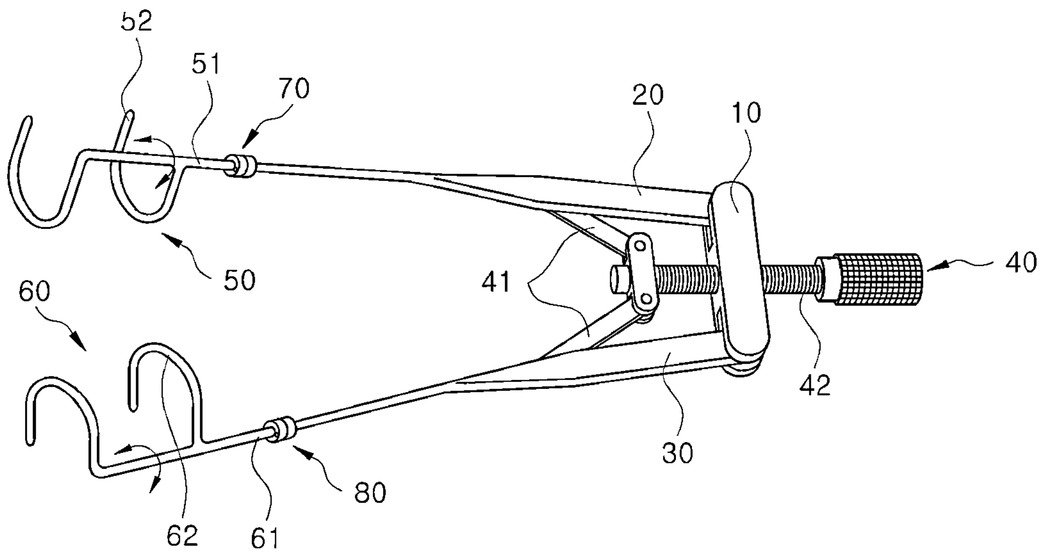
FIG. 1 is a perspective view illustrating an eyelid speculum according to a first embodiment of the present disclosure.

The advantages and features of the present disclosure, and the method of achieving them, will be clarified by referring to the embodiments described in detail below together with the attached drawings. However, the present disclosure is not limited to the embodiments disclosed below and may be implemented in various different forms, and these embodiments are provided only to ensure that the disclosure of the present disclosure is complete and to fully inform those skilled in the art, to which the present disclosure pertains, of the scope of the present disclosure, and the present disclosure is defined only by the scope of the claims.

Unless otherwise defined, all terms (including technical and scientific terms) used in the specification may be used in a meaning that can be commonly understood by those skilled in the art, to which the present disclosure pertains. In addition, the terms defined in a commonly used dictionary shall not be ideally or excessively interpreted unless explicitly specifically defined.

Prior to a description of the present disclosure, in various embodiments, components having the same configuration will be representatively described in a first embodiment by using the same reference numerals, and in the other embodiments, components that are different from those of the first embodiment will be described.

Hereinafter, embodiments of the present disclosure will be described in detail with reference to the accompanying drawings.

Figure 2:
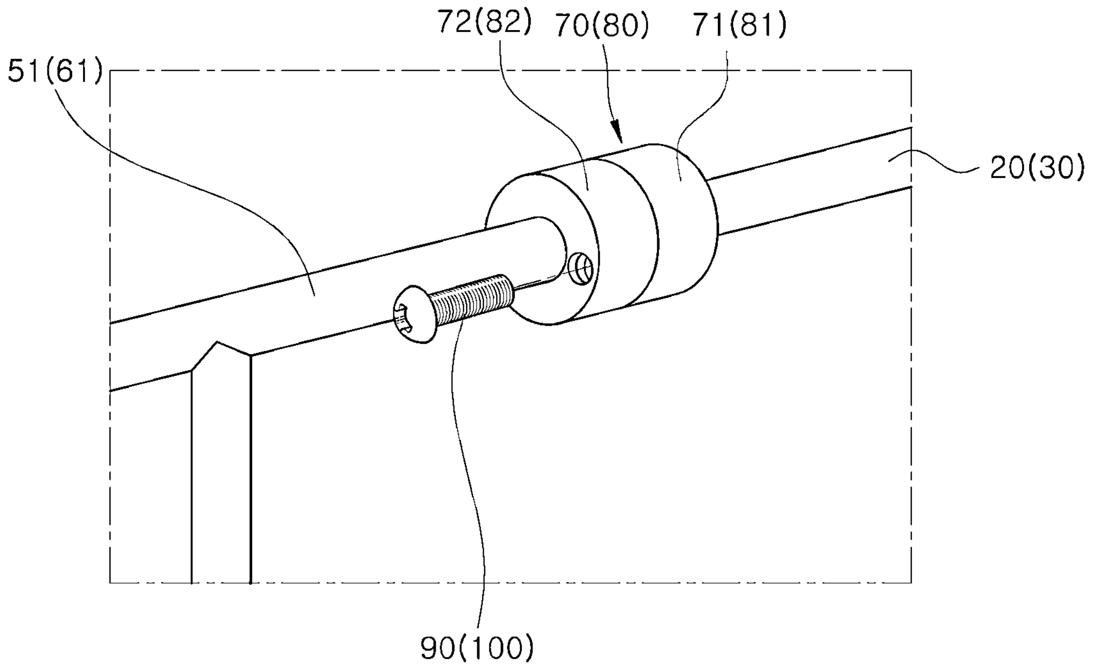
FIG. 2 is a perspective view illustrating a first hinge part and a first locking part (a second hinge part and a second locking part) of an eyelid speculum according to a first embodiment of the present disclosure.
Figure 3:
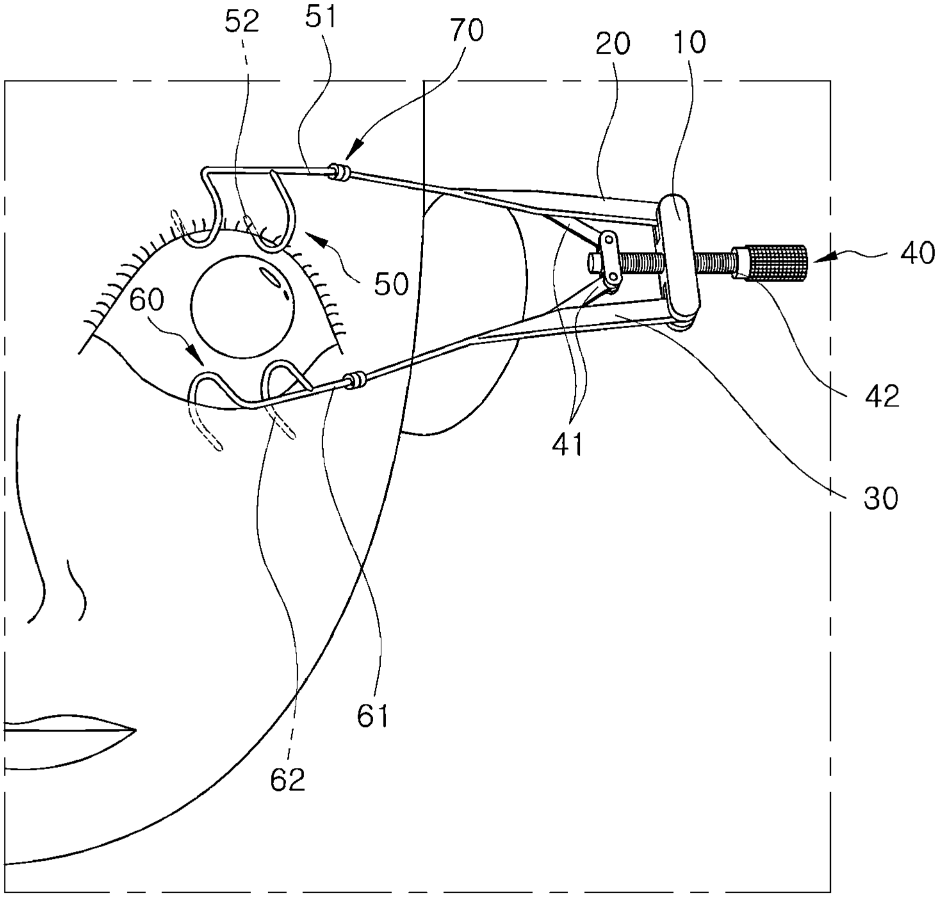
FIG. 3 is a perspective view illustrating a state, in which an eyelid speculum according to a first embodiment of the present disclosure widens an upper eyelid and a lower eyelid.

FIG. 1 is a perspective view illustrating an eyelid speculum according to a first embodiment of the present disclosure, FIG. 2 is a perspective view illustrating a first hinge part and a first hinge part and a first locking part (a second hinge part and a second locking part) of the eyelid speculum according to the first embodiment of the present disclosure, and FIG. 3 is a perspective view illustrating a state, in which the eyelid speculum according to the first embodiment of the present disclosure widens an upper eyelid and a lower eyelid.

As illustrated in FIGS. 1 to 3, the eyelid speculum according to the first embodiment of the present disclosure may include a frame 10, a first rotary arm 20, a second rotary arm 30, a movement part 40, a first support arm 50, and a second support arm 60.

The frame 10 is a basic body of the present disclosure. The first rotary arm 20 and the second rotary arm 30 may be coupled to opposite sides of the frame 10 to be rotatable.

The first rotary arm 20 may be coupled to one side of the frame 10 to be rotatable, and the second rotary arm 30 may be coupled to an opposite side of the frame 10 to be rotatable. The first support arm 50 may be coupled to a distal end of the first rotary arm 20 to be rotatable, and the second support arm 60 may be coupled to a distal end of the second rotary arm 30 to be rotatable. Accordingly, when the first rotary arm 20 and the second rotary arm 30 are moved in a direction, in which they become more distant from each other, the first support arm 50 and the second support arm 60 may also be moved in a direction, in which they become more distant from each other, and the first rotary arm 20 and the second rotary arm 30 may also be moved in a direction, in which they become closer to each other. As an example, the first rotary arm 20 and the second rotary arm 30 may be disposed to be symmetrical to each other with respect to the frame 10.

The movement part 40 serves to move the first rotary arm 20 and the second rotary arm 30 in a direction, in which they become closer to or more distant from each other. The movement part 40 may include a handle 41 and two links 42.

The handle 41 may be disposed between the first rotary arm 20 and the second rotary arm 30 in the frame 10, and may be coupled to reciprocate in a vertical direction that is perpendicular to a central axis of the frame 10. For example, the handle 41 may be screw-coupled to the frame 10 to reciprocate in a vertical direction that is perpendicular to the central axis of the frame 10. Here, a screw hole that is screw-coupled to the handle 41 may be formed in the frame 10, and the handle 41 may have a screw shaft shape.

The two links 42 may serve to convert a reciprocation of the handle 41 in the frame 10 into a movement in a direction, in which the first rotary arm 20 and the second rotary arm 30 become more distant from or closer to each other. To this end, sides of the two links 42 may be hinge-coupled to opposite sides of the handle 41, respectively, and opposite sides of the two links 42 may be hinge-coupled to the inside of the first rotary arm 20 and the inside of the second rotary arm 30, respectively.

As an example, when the handle 41 is moved in a direction, in which it becomes closer to the two links 42, the two links 42 may be moved in a direction, in which they become more distant from each other, and the first rotary arm 20 and the second rotary arm 30 may be moved in a direction, in which they become more distant from each other.

As an example, when the handle 41 is moved in a direction, in which it becomes more distant from the two links 42, the two links 42 may be moved in a direction, in which they become closer to each other, and the first rotary arm 20 and the second rotary arm 30 may be moved in a direction, in which they become closer to each other.

Meanwhile, the two links 42 may be disposed to be symmetrical to each other with respect to the frame 10.

The first support arm 50 may be coupled to the first rotary arm 20 to be rotatable, and may serve to support the upper eyelid. The first support arm 50 may include a first connection part 51 and a first curved part 52.

The first connection part 51 may be coupled to the first rotary arm 20 to be rotatable. As an example, the first connection part 51 may be coaxially coupled to the first rotary arm 20. As another example, the first connection part 51 may be misaligned with the first rotary arm 20.

The first curved part 52 extends from the first connection part 51 in an arc shape, and may be inserted into the inside of the upper eyelid to support the upper eyelid. Here, the inside of the upper eyelid may be between an inner surface of the upper eyelid and an outer surface of the eyeball.

As an example, a distal end of the first curved part 52 may protrude in a direction, in which it becomes more distant from the second support arm 60.

The second support arm 60 may be coupled to the second rotary arm 30 to be rotatable, and may serve to support the lower eyelid. The second support arm 60 may include a second connection part 61 and a second curved part 62.

The second connection part 61 may be coupled to the second rotary arm 30 to be rotatable. As an example, the second connection part 61 may be coaxially coupled to the second rotary arm 30. As another example, the second connection part 61 may be misaligned with the second rotary arm 30.

The second curved part 62 extends from the second connection part 61 in an arc shape, and may be inserted into the inside of the lower eyelid to support the lower eyelid. Here, the inside of the lower eyelid may be between an inner surface of the lower eyelid and an outer surface of the eyeball.

As an example, a distal end of the second curved part 62 may protrude in a direction, in which it becomes more distant from the first support arm 50.

As an example, when the first curved part 52 and the second curved part 62 are inserted into the inside of the upper eyelid and the inside of the lower eyelid, respectively, the first curved part 52 may be rotated to be aligned on the inside of the upper eyelid as the upper eyelid pushes the first curved part 52, and the second curved part 62 may be rotated to be aligned on the inside of the lower eyelid as the lower eyelid pushes the second curved part 62. Accordingly, when the first curved part 52 and the second curved part 62 are inserted into the inside of the upper eyelid and the inside of the lower eyelid, respectively, a contact between the first curved part 52 and the cornea may be prevented, and a contact between the second curved part 62 and the cornea may be prevented. For reference, the first curved part 52 may be rotated by a relative rotation of the first connection part 51 with respect to the first rotary arm 20. Furthermore, the second curved part 62 may be rotated by a relative rotation of the second connection part 61 with respect to the second rotary arm 30.

Thereafter, when the first curved part 52 inserted into the inside of the upper eyelid and the second curved part 62 inserted into the inside of the lower eyelid are discharged, the first curved part 52 and the second curved part 62 may be discharged in a state, in which the first curved part 52 is rotated in a direction, in which it faces the upper eyelid, to be spaced apart from the cornea, and the second curved part 62 is rotated in a direction, in which it faces the lower eyelid, to be spaced apart from the cornea. As a result, when the first curved part 52 inserted into the inside of the upper eyelid and the second curved part 62 inserted into the inside of the lower eyelid are discharged, a contact between the first curved part 52 and the cornea may be prevented, and a contact between the second curved part 62 and the cornea may be prevented.

As an example, a plurality of first curved parts 52 may be provided, and the plurality of first curved parts 52 may be arranged along the first connection part 51. According to another example, referring to FIG. 1, two first curved part 52 may be provided, and the two first curved parts 52 may be arranged along the first connection part 51.

As an example, a plurality of second curved parts 62 may be provided, and the plurality of second curved parts 62 may be arranged along the second connection part 61. As another example, referring to FIG. 1, two second curved parts 62 may be provided, and the two second curved parts 62 may be arranged along the second connection part 61.

The eyelid speculum according to the first embodiment of the present disclosure may include a first hinge part 70, a second hinge part 80, a first locking part 90, and a second locking part 100.

The first hinge part 70 may couple the first support arm 50 with respect to the first rotary arm 20 such that the first support arm 50 is relatively rotated in a circumferential direction of the first rotary arm 20. Referring to FIG. 1, the first hinge part 70 may couple the first connection part 51 with respect to the first rotary arm 20 such that the first connection part 51 is rotated in a circumferential direction of the first rotary arm 20.

The first hinge part 70 may include a first fixing shaft 71 and a first hinge shaft 72. Here, the first fixing shaft 71 may be coupled to a distal end of the first rotary arm 20. Furthermore, the first hinge shaft 72 may be coupled to the first fixing shaft 71 to be rotated in a circumferential direction of the first rotary arm 20 and may be coupled to a distal end of the first connection part 51. For example, the first fixing shaft 71 and the first hinge shaft 72 may have annular shapes.

The second hinge part 80 may couple the second support arm 60 with respect to the second rotary arm 30 such that the second support arm 60 is relatively rotated in a circumferential direction of the second rotary arm 30. Referring to FIG. 1, the second hinge part 80 may couple the second connection part 61 with respect to the second rotary arm 30 such that the second connection part 61 is rotated in a circumferential direction of the second rotary arm 30.

The second hinge part 80 may include a second fixing shaft 81 and a second hinge shaft 82. Here, the second fixing shaft 81 may be coupled to a distal end of the second rotary arm 30. Furthermore, the second hinge shaft 82 may be coupled to the second fixing shaft 81 to be rotated in a circumferential direction of the second rotary arm 30 and may be coupled to a distal end of the second connection part 61. For example, the second fixing shaft 81 and the second hinge shaft 82 may have annular shapes.

The first locking part 90 may serve to lock or unlock the first support arm 50 to or from the first rotary arm 20.

A first bolt that is screw-coupled to the first hinge shaft 72 of the first hinge part 70 to be fastened or unfastened to or from the first fixing shaft 71 of the first hinge part 70 may be used as the first locking part 90. For example, when the first bolt is fastened to the first fixing shaft 71, the first support arm 50 may be locked to the first rotary arm 20 as the first hinge shaft 72 and the first fixing shaft 71 are locked. Furthermore, when the first bolt is unfastened from the first fixing shaft 71, the first hinge shaft 72 and the first fixing shaft 71 may be unlocked, and thus, the first support arm 50 may be unlocked from the first rotary arm 20.

The second locking part 100 may serve to lock or unlock the second support arm 60 to or from the second rotary arm 30.

A second bolt that is screw-coupled to the second hinge shaft 82 of the second hinge part 80 to be fastened or unfastened to or from the second fixing shaft 81 of the second hinge part 80 may be used as the second locking part 90. For example, when the second bolt is fastened to the second fixing shaft 81, the second support arm 60 may be locked to the second rotary arm 30 as the second hinge shaft 82 and the second fixing shaft 81 are locked. Furthermore, when the second bolt is unfastened from the second fixing shaft 81, the second hinge shaft 82 and the second fixing shaft 81 are unlocked, and thus, the first support arm 50 may be unlocked from the first rotary arm 20.

Hereinafter, a process of widening the upper eyelid and the lower eyelid by the eyelid speculum according to the first embodiment of the present disclosure will be described. The following process may be performed by an operator or a robot arm.

First, as the first curved part 52 of the first support arm 50 and the second curved part 62 of the second support arm 60 are inserted into the inside of the upper eyelid and the inside of the lower eyelid, respectively. In this case, as the upper eyelid pushes the first curved part 52, the first curved part 52 is rotated to be aligned on the inside the upper eyelid, and as the lower eyelid pushes the second curved part 62, the second curved part 62 may be rotated to be aligned on the inside of the lower eyelid. Accordingly, when the first curved part 52 and the second curved part 62 are inserted into the inside of the upper eyelid and the inside of the lower eyelid, respectively, a contact between the first curved part 52 and the cornea may be prevented and a contact between the second curved part 62 and the cornea may be prevented as the first curved part 52 and the second curved part 62 are aligned on the inside of the upper eyelid and the inside of the lower eyelid, respectively.

Subsequently, when necessary, an angle, at which the first curved part 52 connected to the first connection part 51 supports the upper eyelid, may be adjusted by rotating a first connection part 50 of the first support arm 50 through the first hinge part 70, and an angle, at which the second curved part 62 connected to the second connection part 61 supports the lower eyelid, may be adjusted by the second connection part 61 and the second curved part 62 of the second support arm 60 through the second hinge part 80.

Next, the first locking part 90 locks the first connection part 51 to the first rotary arm 20, and the second locking part 100 locks the second connection part 61 to the second rotary arm 30. As a result, both of the angle, at which the first curved part 52 supports the upper eyelid, and the angle, at which the second curved part 62 supports the lower eyelid, may be fixed.

Thereafter, the movement part 40 moves the first rotary arm 20 and the second rotary arm 30 in a direction, in which they become more distant from each other. In this case, as the first connection part 51 and the second connection part 61 are moved in a direction, in which they become more distant from each other, and the first curved part 52 supported by the upper eyelid and the second curved part 62 supported by the lower eyelid are also moved in a direction, in which they become more distant from each other, so that the upper eyelid and the lower eyelid are widened. In this case, because a field of view for the eye surgery is secured, the eye surgery may proceed.

Thereafter, when the first curved part 52 inserted into the inside the upper eyelid and the second curved part 62 inserted into the inside the lower eyelid is discharged, the movement part 40 moves the first rotary arm 20 and the second rotary arm 30 in a direction, in which they become closer to each other in a state, in which the first curved part 52 is rotated in a direction, in which it faces the upper eyelid to be spaced apart from the cornea, and the second curved part 62 is rotated in a direction, in which it faces the lower eyelid to be spaced apart from the cornea. In this case, the first connection part 51 and the second connection part 61 are moved in a direction, in which they become closer to each other, and the first curved part 52 supported by the upper eyelid and the second curved part 62 supported by the lower eyelid are move in a direction, in which they become closer to each other while being spaced apart from the corona, and the first curved part 52 and the second curved part 62 may be discharged from the inside of the upper eyelid and the inside of the lower eyelid, respectively. As a result, when the first curved part 52 inserted into the inside of the upper eyelid and the second curved part 62 inserted into the inside of the lower eyelid are discharged, a contact between the first curved part 52 and the cornea may be prevented, and a contact between the second curved part 62 and the cornea may also be prevented.

Figure 4:
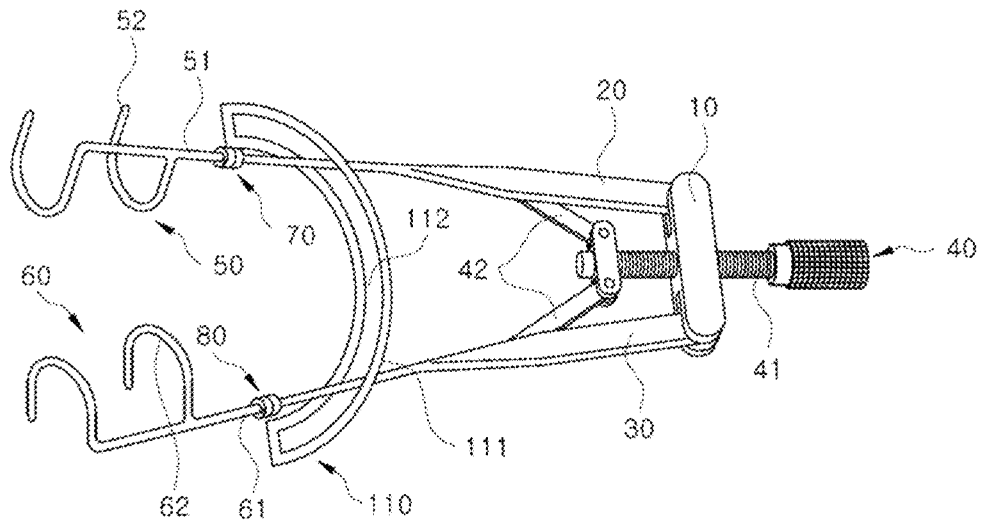
FIG. 4 is a perspective view illustrating an eyelid speculum according to a second embodiment of the present disclosure.
Figure 5:
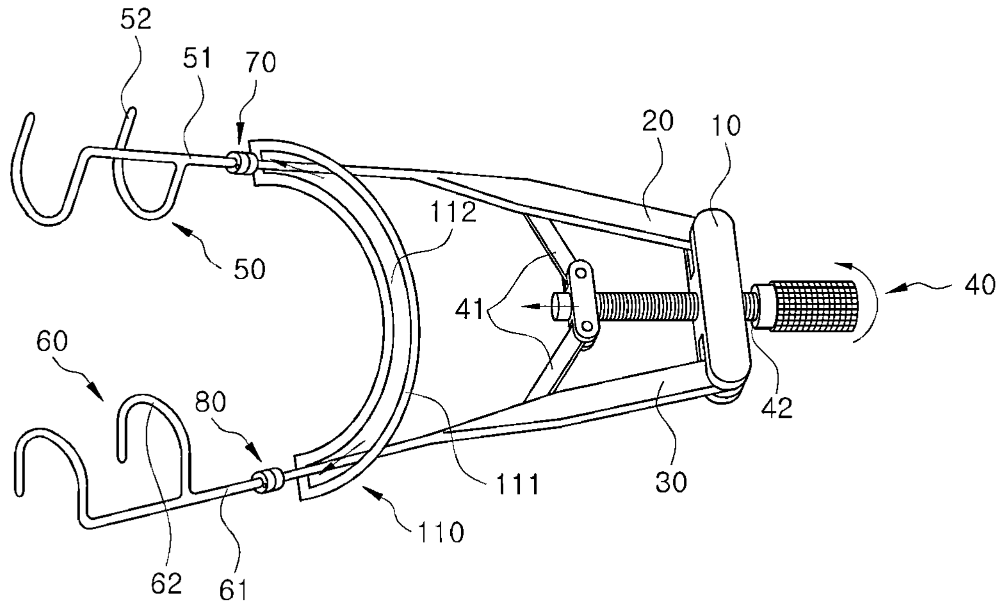
FIG. 5 is a perspective view illustrating a state, in which a first curved part and a second curved part are moved through a guide rail of an eyelid speculum according to a second embodiment of the present disclosure.
Figure 6:
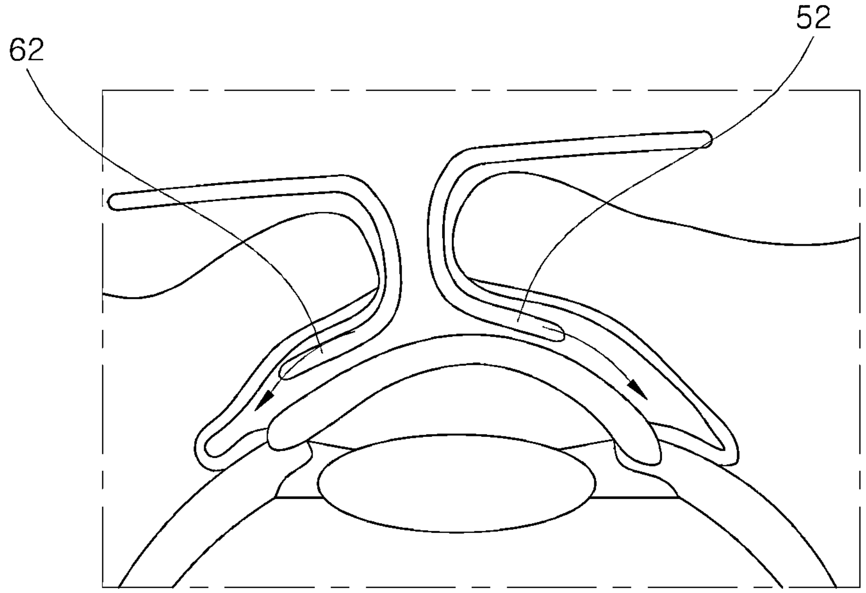
FIG. 6 is a cross-sectional view illustrating a state, in which a first curved part and a second curved part are moved along a circumference of an eyeball through a guide rail of an eyelid speculum according to a second embodiment of the present disclosure.

FIG. 4 is a perspective view illustrating an eyelid speculum according to a second embodiment of the present disclosure, FIG. 5 is a perspective view illustrating a state, in which a first curved part and a second curved part are moved through a guide rail of the eyelid speculum according to the second embodiment of the present disclosure, and FIG. 6 is a cross-sectional view illustrating a state, in which the first curved part and the second curved part are moved along a circumference of an eyeball through the guide rail of the eyelid speculum according to a second embodiment of the present disclosure.

As illustrated in FIGS. 4 to 6, the eyelid speculum according to the second embodiment of the present disclosure may further include a guide rail 110.

The guide rail 110 may serve to guide movement paths of the first connection part 51 and the second connection part 61 to paths in an arc shape corresponding to a circumference of the eyeball so that the first curved part 52 and the second curved part 62 are moved along the circumference of the eyeball when the first curved part 52 supported by the inside of the upper eyelid and the second curved part supported by the inside of the lower eyelid are moved in a direction, in which the upper eyelid and the lower eyelid are widened or gathered. The guide rail 110 may include a rail body 111 and a rail hole 112.

The rail body 111 is a basic body of the guide rail 110. For example, the rail body 111 may have an arc shape. Furthermore, the rail body 111 may be supported by a facial surface or an outer structure, when necessary.

The rail hole 112 may be formed to pass through the rail body 111 in an arc shape corresponding to the circumference of the eyeball, and the first connection part 51 and the second connection part 61 may be inserted thereinto. Here, the first connection part 51 and the second connection part 61 may be moved along the rail hole 112 and may be moved along an arc-shaped path corresponding to the circumference of the eyeball.

Hereinafter, a process of widening an eye by the eyelid speculum according to the second embodiment of the present disclosure will be described.

First, as the first curved part 52 of the first support arm 50 and the second curved part 62 of the second support arm 60 are inserted into the inside of the upper eyelid and the inside of the lower eyelid, respectively. In this case, as the upper eyelid pushes the first curved part 52, the first curved part 52 is rotated to be aligned on the inside the upper eyelid, and as the lower eyelid pushes the second curved part 62, the second curved part 62 may be rotated to be aligned on the inside of the lower eyelid. Accordingly, when the first curved part 52 and the second curved part 62 are inserted into the inside of the upper eyelid and the inside of the lower eyelid, respectively, a contact between the first curved part 52 and the cornea may be prevented and a contact between the second curved part 62 and the cornea may be prevented as the first curved part 52 and the second curved part 62 are aligned on the inside of the upper eyelid and the inside of the lower eyelid, respectively.

Subsequently, when necessary, an angle, at which the first curved part 52 connected to the first connection part 51 supports the upper eyelid, may be adjusted by rotating the first connection part 50 of the first support arm 50 through the first hinge part 70, and an angle, at which the second curved part 62 connected to the second connection part 61 supports the lower eyelid, may be adjusted by rotating the second connection part 61 and the second curved part 62 of the second support arm 60 through the second hinge part 80.

Next, the first locking part 90 locks the first connection part 51 to the first rotary arm 20, and the second locking part 100 locks the second connection part 61 to the second rotary arm 30. As a result, both of the angle, at which the first curved part 52 supports the upper eyelid, and the angle, at which the second curved part 62 supports the lower eyelid, may be fixed.

Thereafter, the movement part 40 moves the first rotary arm 20 and the second rotary arm 30 in a direction, in which they become more distant from each other. In this case, the first connection part 51 and the second connection part 61 are moved along the rail hole of the guide rail 110 in an arc-shaped path corresponding to the circumference of the eyeball, and the first curved part 52 supported by the upper eyelid and the second curved part 62 supported by the lower eyelid are also moved in an arc-shaped path corresponding to the circumference of the eyeball. As a result, as movement distances of the first curved part 52 and the second curved part 62 increase, the first curved part 52 and the second curved part 62 are firmly supported by the inside of the upper eyelid and the inside of the lower eyelid, respectively, so that the first curved part 52 and the second curved part 62 may be prevented from being separated from the upper eyelid and the lower eyelid, respectively. Because the field of view for the eye surgery is secured in this process, the eye surgery may proceed.

Thereafter, when the first curved part 52 inserted into the inside of the upper eyelid and the second curved part 62 inserted into the inside of the lower eyelid are discharged, the movement part 40 moves the first rotary arm 20 and the second rotary arm 30 in a direction, in which they become closer to each other. In this case, the first connection part 51 and the second connection part 61 are moved along the rail hole of the guide rail 110 in an arc-shaped path corresponding to the circumference of the eyeball, and the first curved part 52 supported by the upper eyelid and the second curved part 62 supported by the lower eyelid are also moved in an arc-shaped path corresponding to the circumference of the eyeball, and the first curved part 52 and the second curved part 62 may be discharged from the inside of the upper eyelid and the inside of the lower eyelid, respectively. As a result, when the first curved part 52 inserted into the inside of the upper eyelid and the second curved part 62 inserted into the inside of the lower eyelid are discharged, a contact between the first curved part 52 and the cornea may be prevented, and a contact between the second curved part 62 and the cornea may also be prevented.

Figure 7:
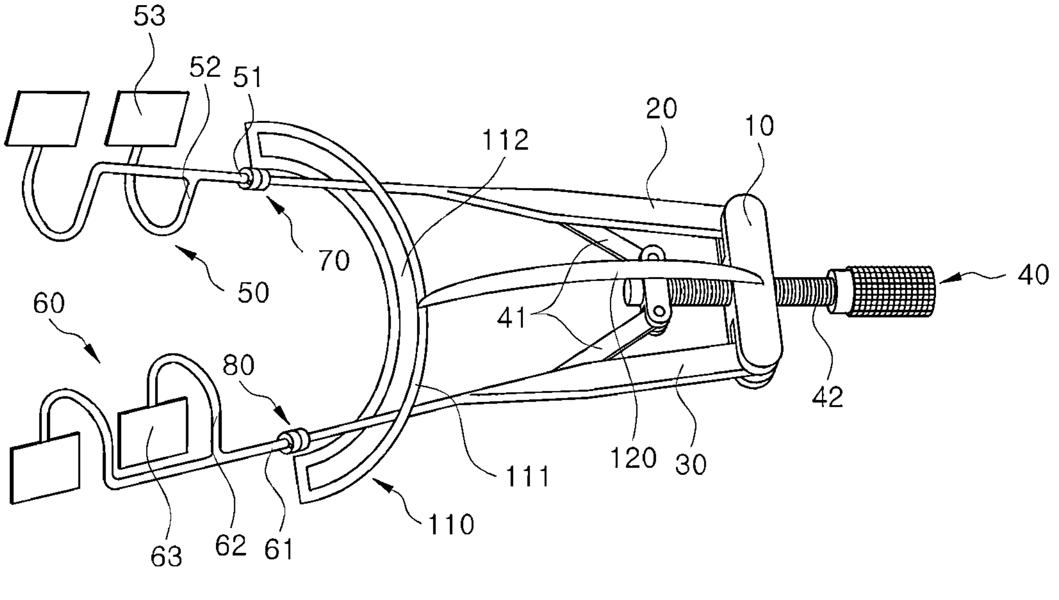
FIG. 7 is a perspective view illustrating an eyelid speculum according to a third embodiment of the present disclosure.

FIG. 7 is a perspective view illustrating an eyelid speculum according to a third embodiment of the present disclosure.

As illustrated in FIG. 7, unlike in the second embodiment, the eyelid speculum according to the third embodiment may further include a connector 120 that connects the body and the frame 10.

In an embodiment, the rail body 111 may be supported by the frame 10 through the connector 120.

In an embodiment, a first pad 53 having a width that is greater than that of the first curved part 52 may be provided at a distal end of the first curved part 52, and a second pad 63 having a width that is greater than that of the second curved part 62 may be provided at a distal end of the second curved part 62.

According to the present disclosure, the eyelid speculum according to an embodiment of the present disclosure prevents damage to the corona and the occurrence of eyelid ptosis when the eye is widened.

Furthermore, according to the eyelid speculum according to an embodiment of the present disclosure, the guide rail guides the movement paths of the first connection part and the second connection part to the arc-shaped path corresponding to the circumference of the eyeball so that the first curved part and second curved part are moved along the circumference of the eyeball when the first curved part supported by the upper eyelid and the second curved part supported by the lower eyelid are moved in the direction, in which the upper eyelid and the lower eyelid are widened or gathered, and thus, the first curved part and the second curved part may be prevented from being separated from the upper eyelid and the lower eyelid, respectively.

In the existing eyelid speculum, as the upper eyelid and lower eyelid are widened more to secure the field of view of the surgery, the speculum deviates from the upper eyelid and the lower eyelid more often. This is because the upper eyelid and lower eyelid are widened more, the upper eyelid and lower eyelid are separated from the eyeball more. However, in the present disclosure, the first and second curved parts are moved along the circumference of the eyeball, and the upper eyelid and the lower eyelid are widened, so that the eyelids are not loosened even when they are widened much to secure the field of view of the surgery, and rather, the eyelid is fastened more tightly. Accordingly, the upper eyelid and lower eyelid may be widened with certainty.

Furthermore, the present disclosure may make a double eyelid during the eye is widened, and it is advantageous cosmetically. This is because directions of forces of the first curved part and the second curved part, which widen the upper eyelid and the lower eyelid, are the same as directions of forces during a double eyelid surgery, and it is similar to the effect of picking-up with a double eyelid tape.

Furthermore, the present disclosure may secure a more effective field of view of the surgery. That is, because the upper and lower eyelid are widened while the first curved part and the second curved part are moved along the circumference of the eyeball, a wide field of view of the surgery than that of the existing eyelid speculum may be secured, so that a more effective field of view of the surgery may be secured. This may be explained geometrically.

Furthermore, the present disclosure may prevent a damage to the corona. The existing speculum has a structure, in which two metal bars are inserted into the inside of the upper eyelid and the inside of the lower eyelid to widen the eyelids. However, two metal bars often touch the corona located at a center of the eyeball to cause a damage to the cornea. Accordingly, there is an inconvenience that the operator has to always be careful to prevent a damage to the cornea, and the process of inserting the speculum by lifting the eyelids to prevent the damage to the cornea itself is vulnerable to a damage to the eyelids. On the other hand, according to the present disclosure, when the first curved part and the second curved part are inserted into the upper eyelid and the lower eyelid, respectively, there is no risk of damaging the corona because they are inserted into peripheries (e.g., empty spaces of a nose and ears: a media conjunctiva and a lateral conjunctiva) with no cornea. Furthermore, it is more advantageous in securing the field of view of the surgery because it widens better the empty spaces on the nose and ears, which are often used for a vitreous resection.

Furthermore, according to the present disclosure, when the upper eyelid and the lower eyelid are widened, the backbone located on the outside is rotated simultaneously. Accordingly, the upper eyelid and the lower eyelid are automatically externally rotated, so that the speculum may be better mounted on the eyeball and the eyelids may be widened efficiently. This is because, to widen the upper eyelid and lower eyelid well, the distal end of the upper eyelid and the distal end of the lower eyelid have to be externally rotated to be turned outward.

The eyelid speculum according to one embodiment of the present disclosure may prevent damage to the cornea and the ptosis when the eye is widened.

Furthermore, according to the eyelid speculum according to an embodiment of the present disclosure, the guide rail guides the movement paths of the first connection part and the second connection part to the arc-shaped path corresponding to the circumference of the eyeball so that the first curved part and second curved part are moved along the circumference of the eyeball when the first curved part supported by the upper eyelid and the second curved part supported by the lower eyelid are moved in the direction, in which the upper eyelid and the lower eyelid are widened or gathered, and thus, the first curved part and the second curved part may be prevented from being separated from the upper eyelid and the lower eyelid, respectively.

Effects of the present disclosure are not limited to the effects mentioned above, and other effects not mentioned will be clearly understood by those skilled in the art from the following description.

Although the present disclosure has been described above with reference to the attached drawings, it will be understood by those skilled in the art that the present disclosure may be implemented in other specific forms without changing the technical spirit or essential features thereof. Therefore, it should be understood that the present disclosure described above is illustrative in all respects and not restrictive.

What is claimed is:

1. An eyelid speculum comprising:

a frame;

a first rotary arm coupled to one side of the frame to be rotatable;

a second rotary arm coupled to an opposite side of the frame to be rotatable;

a movement part configured to move the first rotary arm and the second rotary arm such that the first rotary arm and the second rotary arm are moved in a direction, in which they become closer to or more distant from each other;

a first support arm coupled to the first rotary arm to be rotatable, and configured to support an upper eyelid;

a second support arm coupled to the second rotary arm, and configured to support a lower eyelid, wherein the first support arm includes:

a first connection part coupled to the first rotary arm to be rotatable; and a first curved part extending from the first connection part in an arc shape, and configured to be inserted into an inside of the upper eyelid to support the upper eyelid, and wherein the second support arm includes:

a second connection part coupled to the second rotary arm to be rotatable; and a second curved part extending from the second connection part in an arc shape, and configured to be inserted into an inside of the lower eyelid to support the lower eyelid; and a guide rail configured to, when the first curved part and the second curved part are moved to widen or gather the upper eyelid and the lower eyelid, guide movement paths of the first connection part and the second connection part to a guide in an arc shape corresponding to a circumference of an eyeball such that the first curved part and the second curved part are moved along the circumference of the eyeball, wherein the guide rail includes:

a rail body; and a rail hole formed to pass through the rail body in an arc shape, and into which the first connection part and the second connection part are inserted.

2. The eyelid speculum of claim 1, wherein when the first curved part and the second curved part are inserted into the inside of the upper eyelid and the inside of the lower eyelid, respectively, the first curved part is rotated to be aligned on the inside of the upper eyelid and the second curved part is rotated to be aligned on the inside of the lower eyelid.

3. The eyelid speculum of claim 1, wherein a plurality of first curved parts are provided, and the plurality of first curved parts are arranged along the first connection part, and wherein a plurality of second curved parts are provided, and the plurality of second curved parts are arranged along the second connection part.

* * * * *